United States Patent [19]

Ward et al.

[11] Patent Number: 5,384,174
[45] Date of Patent: Jan. 24, 1995

[54] ADHESIVE SHEET

[75] Inventors: William J. Ward, Hull; Jil F. Philistin-Rabaud, Anlaby, both of United Kingdom

[73] Assignee: Smith & Nephew plc, United Kingdom

[21] Appl. No.: 24,852

[22] Filed: Feb. 26, 1993

Related U.S. Application Data

[63] Continuation of Ser. No. 603,700, filed as PCT/GB89/00563, May 22, 1989, abandoned.

[30] Foreign Application Priority Data

May 21, 1988 [GB] United Kingdom ............... 8812096

[51] Int. Cl.⁶ .................................................. B32B 9/00
[52] U.S. Cl. ..................................... 428/40; 428/343; 428/352; 206/440; 206/441
[58] Field of Search .................... 428/343, 40, 352; 206/440, 441

[56] References Cited

U.S. PATENT DOCUMENTS

| | | | |
|---|---|---|---|
| 3,645,835 | 2/1972 | Hodgson | 161/146 |
| 3,925,584 | 12/1975 | Suzuki et al. | 428/40 |
| 4,702,948 | 10/1987 | Sieber-Gadient | 428/40 |
| 4,767,654 | 8/1988 | Riggsbee | 428/40 |
| 4,815,457 | 3/1989 | Mazars et al. | 128/155 |

Primary Examiner—Patrick J. Ryan
Assistant Examiner—Kam F. Lee
Attorney, Agent, or Firm—Rosenman & Colin

[57] ABSTRACT

An adhesive sheet material for use comprises a backing layer which has upon at least a portion of one surface a pressure sensitive adhesive layer. A removable release liner covers the adhesive layer and a support layer is attached to the backing layer on the surface remote from the pressure sensitive adhesive layer. The stripping load required to separate the release liner from the adhesive layer is greater than the stripping load required to separate the support layer from the backing layer. As the release liner is stiffer than the support layer then the release liner can be removed from the adhesive without disturbing the support layer. The support layer is conformable enough to remain attached to the sheet when adhered to the skin. Adhesive sheets in the form of ostomy flanges and IV dressings are described.

13 Claims, 3 Drawing Sheets

ADHESIVE SHEET

This is a continuation application of U.S. Ser. No. 07/603,700, filed as PCT/GB89/00563, May 22, 1989, now abandoned.

The present invention relates to an adhesive sheet material for use on the skin which comprises a backing layer which has on one surface a pressure sensitive adhesive layer covered by a removable release liner and attached to the other surface a support layer. The sheet material may be used as a wound dressing, a dressing for an indwelling catheter or if the central area of the sheet is removed as an ostomy flange for retaining a bag around a stoma.

Adhesive sheet materials have been used as dressings for many years. These products comprise a thin, filmic, moisture vapour permeable polymeric material coated on one surface with an adhesive. The sheet was presented for use with a protector layer over the adhesive and adhesive-free handles at a pair of opposed edges. Subsequently alternative modes of presentation were introduced to ease application of the thin filmic product for the inexperienced particularly in an effort to prevent the dressing creasing and adhering to itself during application. If this occurs then the dressing must be discarded. One such mode of presentation required the presence of a carrier film usually of a material stiffer than the adhesive coated film adhered to the non-adhesive surface of that film. To apply such dressings the release liner was removed, the adhesive coated film was adhered to the patient and then the carrier removed. Dressings of this type are described in for example United Kingdom Patent No. 2120104, European Patents Nos. 51935, 66899 and 81990 and U.S. Pat. Nos. 4,372,303, 4,374,520 and 4,545,371.

A dressing known as Tegaderm (Trade mark) has been introduced which Is provided with a frame of cardboard attached to the non-adhesive coated surface of the dressing to facilitate its application. This product is said to be within the ambit of European Patent No. 51935. The dressing claimed in that patent requires that a releasable layer which comprises the frame is attached more tenaciously to the non-adhesive surface of the film than is a release liner attached to the adhesive surface of the dressing. This ensures that the release liner may be removed from the adhesive surface with reduced risk of disturbing the dressing held on the releasable layer. However, there is a risk that because the releasable layer is adhered strongly to the dressing then when it is removed it may disturb the dressing on the patient.

Surprisingly it has been found that by using a release liner which is stiffer than the support layer attached to the non-adhesive side of the sheet, the release liner can be allowed to adhere to the adhesive layer more strongly than the support layer adheres to the non-adhesive surface of the sheet and still permit the release liner to be removed without dislodging the support layer from the backing layer. The support layer can be therefore lightly adhered to the film and consequently be easier to remove. This is particularly advantageous when the support layer is in more than one portion for example when it comprises a central portion and a peripheral portion. The central portion may be easily removed so that the sheet material may be adhered to a colostomy bag or the like. The peripheral portion may also comprise two pieces so that they may be removed sequentially unlike the prior art in which the frame is removed in one piece.

Advantageously the release liner may be divided into three portions a large central portion and two end strips so that the large central portion may be removed first. The portions may be separable along a score line or a line of perforations. The end strips may be used to handle the dressing during application and be removed after application of the dressing. The end strips may be specially shaped to facilitate handling.

Accordingly the present invention provides an adhesive sheet material for use on the skin which comprises a backing layer which has upon at least a portion of one surface thereof a pressure sensitive adhesive layer, a removable release liner covering the adhesive layer and a support layer attached to the surface of the backing layer remote from the pressure sensitive adhesive layer wherein the stripping load required to separate the release liner from the adhesive layer is greater than the stripping load required to separate the support layer from the backing layer and the release liner is stiffer than the support layer.

In a preferred embodiment the pressure sensitive adhesive covers essentially the whole of one surface of the backing layer.

Suitably the stripping load required to separate the release liner from the adhesive layer is at least 25% greater, more suitably at least 50% greater and preferably at least 100% greater than the stripping load required to separate the support layer from the backing layer. Suitably the stripping load required to separate the release liner from the adhesive layer is from 5 to 25 gf/cm, more suitably is 8 to 20 gf/cm and is preferably 10 to 18 gf/cm. The stripping load may be measured by the procedure described hereinafter.

The stripping load of the support layer from the backing layer may be measured by taking a sample of the adhesive sheet about 200 mm × 25 mm removing the release liner and adhering the sample to a metal plate. A standard 2 Kg roller is passed three times along the strip and the sample allowed to relax for 5 minutes after rolling. The plate is gripped by the lower jaw of a tensile testing machine. A short length of the support layer is peeled back through 180° so that it may be attached to the upper jaw. The sample is peeled at a rate of 300 mm/min. The results are expressed as average peel force per unit width.

The stripping load may be defined as the average load per unit width of bond line required to separate progressively one layer from another at a separation angle of (approximately) 180° and at a separation rate of 300 mm/min. It is expressed as grams force per cm of width. The stripping load is best measured on a sample of adhesive sheet material prior to forming it into a product. The stripping load of the release liner from the adhesive layer in the product will vary for example if the support layer is present as opposed to absent in the sample to be tested (for example the central portion of the support layer in certain medical products may be absent) thus it is normal to employ a sample in which the support layer and release liner are present.

The stripping load of the release liner from the adhesive layer may be measured by making a sample of adhesive sheet in which the support layer is replaced by an adhesive layer so that this adhesive layer may be adhered to the metal plate. The release liner may be stripped from the adhesive layer using the method described above.

Suitably the stiffness of the release liner and support layer may be measured by taking a strip of the appropriate material, for example a strip 5 cm × 1 cm and clamping one end to an edge of a horizontal surface leaving the remainder of the strip to bend over the edge under its own weight and measuring the deflection of the other end of the strip from the horizontal. The stiffer the strip the less is the deflection.

Suitably the backing layer may comprise any of those materials which are conventionally employed to form thin film surgical dressings. Suitable materials include those described in United Kingdom Patent No. 1280631, European Patents No. 51935, 91800 and 178740. Particularly apt materials are polyurethanes, for example polyester or polyether polyurethanes known as Estanes (Trade mark). Other apt materials are elastomeric polyether polyesters, for example those known as Hytrels (Trade Mark) and polyether polyamides, for example those known as Pebaxes (Trade mark). Other favoured materials include hydrophilic polymers such as hydrophilic polyurethanes including those described in United Kingdom Patent No. 2093190B, especially the polyurethane described in Example 2 therein.

Suitably the backing layer may be moisture vapour permeable and has a moisture vapour transmission rate of at least 500 g/m²/24 h at 37° C. and 100% to 10% relative humidity difference, more suitably at least 1200 g/m²/24 h and preferably at least 1600 g/m²/24 h.

Suitably the backing layer can have as a thickness of from 15 to 100 μm, more suitably 20 to 80 μm and preferably 25 to 50 μm, for example 27.5 μm, 30 μm, 35 μm and 40 μm.

Aptly the pressure sensitive adhesive layer may be formed from an adhesive which is conventionally used for contact with the skin. Suitable adhesives include polyvinyl alkyl ether adhesive and acrylate ester copolymer adhesives. Suitable adhesives are described in United Kingdom Patent No. 1280631 and European Patents Nos. 35399 and 51935. Preferably the adhesive is a polyvinyl ethyl ether adhesive or an acrylate ester copolymer adhesive formed by the compolymerisation of 2-ethylhexyl acrylate, butyl acrylate and acrylic acid.

Suitably the adhesive layer may be from 15 to 65 μm thick, for example 20 to 40 μm thick and is applied at a weight per unit area of 10 to 75 gsm, more suitably 15 to 65 gsm and preferably 25 to 40 gsm.

Suitably the release liner may be a silicone coated release paper. Suitably the release liner may have a weight per unit area of 100 to 140 gsm, and preferably 110 to 130 gsm, for example 120 gsm. The release liner may be present as a single piece or may be divided into two or more pieces for example into three pieces by score cutting through or perforating the release liner to provide a major central portion and two strips on either edge. The central portion of the release liner may be removed first and the side strips used to hold the dressing so as to reduce the risk of touching the exposed adhesive surface of the sheet material.

Suitably the support layer can be formed from a polymeric film or a paper. The support layer may be attached to the backing layer by virtue of casting the backing layer onto the support layer thereby forming an attachment which is easily reversed. Suitably the support layer is a conformable paper of weight 110 to 130 gsm. By conformable is meant that the paper will conform to the contours of a surface to which it is applied. The support layer may be left attached to the backing layer without detracting from the performance of the adhesive sheet material.

Suitably the support layer may carry a pattern of cuts so that different portions of the support layer may be removed without disturbing the remaining portions. Suitably a central portion of the support layer may be removed to leave peripheral portions of the support layer.

In one embodiment the adhesive sheet material may be in the form of an ostomy flange. In one form of flange a central portion of the sheet material may be completely removed or may be partially cut through so that it may be easily removed to form the flange. The support layer then may be itself cut through to form two or more pieces, for example a central usually circular piece and the remaining pieces which are present on the periphery of the sheet. In use the central piece is removed and the flange attached to a bag, for receiving body fluids on the side remote from the adhesive layer. The flange is capable of supporting the bag on the body during use.

In a second embodiment the adhesive sheet material may be in a form suitable for covering an indwelling catheter or cannula. For some forms of treatment it may be necessary to gain access to the vein of a patient using a cannula or needle. The cannula or needle or a catheter may be left in the vein so that repeated access may be gained to the vein. In order to prevent contamination of the injection site it is conveniently covered by a thin filmic adhesive dressing. The adhesive sheet material of the invention may be used. The support layer may then be cut into a different pattern to that employed in the adhesive ostomy flange. Here the central portion may be generally elliptical in shape. In use the central portion may be removed before the sheet is adhered over the injection site and cannula. The peripheral region may be left in place or removed once the sheet is in place.

Suitably the adhesive sheet material has a backing layer and adhesive layer which are translucent and preferably are transparent.

Suitably the support layer and the backing layer may be coextensive and the same shape for example both may be circular. However it is envisaged that the support layer may in certain circumstances be smaller or larger than the backing layer and may also be of a different shape. For example in the embodiment which is a colostomy flange, the support layer may be circular and the backing layer may be rectangular. In this arrangement the circular frame provided by the support layer provides even support around the opening in the bag.

The adhesive sheet material may be prepared by casting a solution of the polymer which is to form the backing layer onto the paper which is to form the support layer. The adhesive is then spread onto the release surface of the paper which is to form the release liner. The adhesive is then brought into contact with the backing layer so that a four layer laminate of support layer, backing layer, adhesive layer and release liner is formed which is the adhesive sheet material of the invention. The laminate is cut to the appropriate size. The support layer may be kiss cut to provide the desired pieces of the support layer. The adhesive liner may then be scored through to form the three portion release liner.

By 'kiss cutting' is meant the cutting of one layer of a laminate without cutting a lower layer. Kiss cutting can be accomplished by use of a die in a platen or rotary die cutting press.

In the embodiment which is in the form of an ostomy flange, a circular hole may be punched out of the centre of the adhesive sheet material or a circular pattern may be cut but leaving two small sections uncut so that prior to use these sections may be broken and the centre of the sheet removed. Suitably the hole size may be 1.5 cm in diameter to 5.0 cm in diameter. Usually, however, the smallest hole size is made and a template provided on the release liner to indicate larger hole sizes.

The adhesive sheet material suitably may have an area equivalent from 5×5 cm to 20 cm×20 cm depending upon the use to which it is put. The adhesive sheet material may be cut to any shape including rectangular, circular, elliptical and the like through circular or oval shaped are preferred. Colostomy flanges and cannula fixation dressings may be conveniently circular or elliptical in shape and have an overall diameter of from 10 to 15 cm.

The adhesive sheet material may be placed in a bacteria-proof pack, sealed and sterilised by conventional methods including using ethylene oxide or by γ-irradiation.

In use the sterile sheet material is removed from the pack, the release liner is removed and the adhesive layer applied to the skin as desired.

Preferred embodiments of adhesive sheets of the present invention will now be described with respect to the drawings which are as follows.

Figure 1:
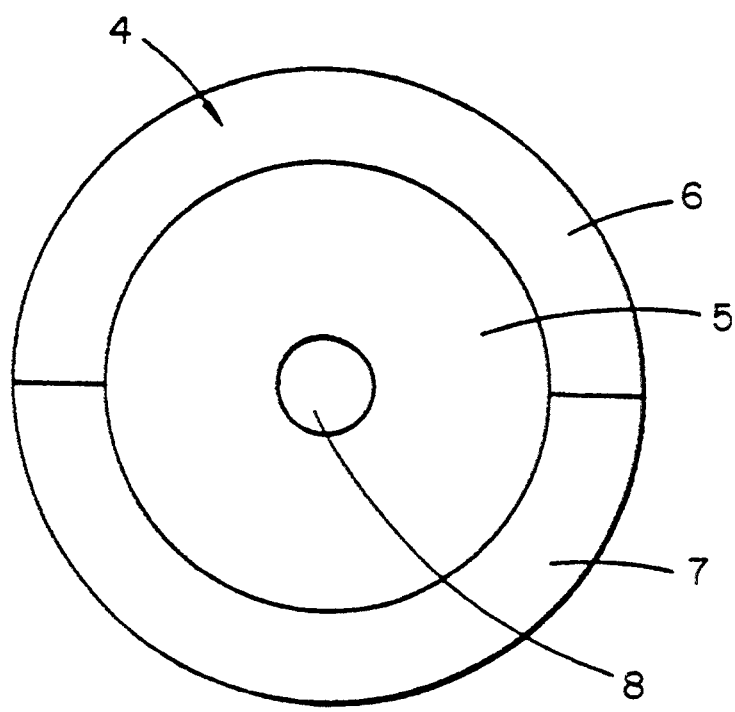
FIG. 1 is an adhesive sheet in the form of an ostomy flange showing the face which is to be joined to an ostomy bag.
Figure 2:
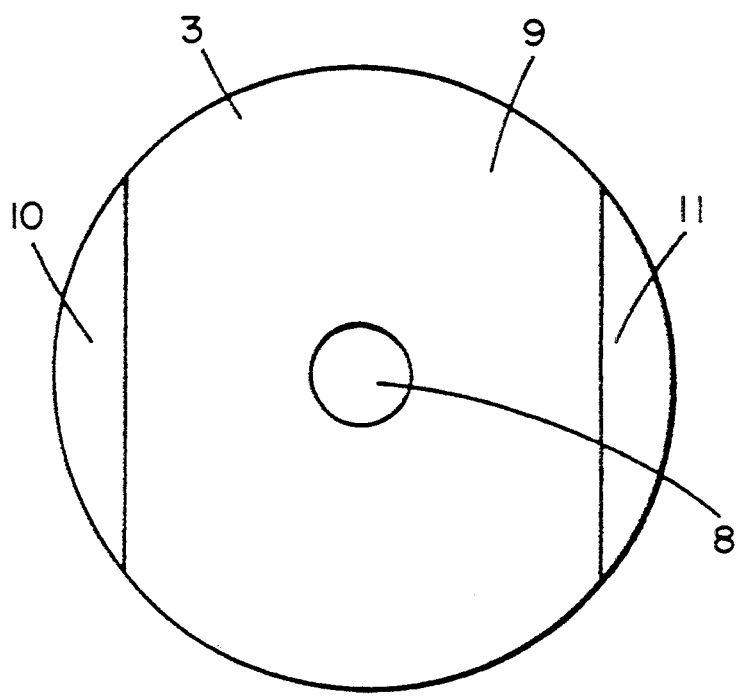
FIG. 2 is the other side of the ostomy flange of FIG. 1.
Figure 3:
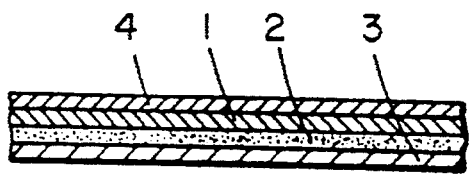
FIG. 3 is a cross-section through the layers making up the ostomy flange.

The pressure sensitive adhesive sheet material shown in FIGS. 1-3 is in the form of an ostomy flange which may be used to retain an ostomy bag around a stoma. FIG. 1 shows the side of the sheet material which is to be Joined to the ostomy bag. The support layer (4) is formed from a release coated paper which has a weight per unit area of 120 gsm. The support layer (4) comprises of three pieces, a central circular piece (5) and two arch-shaped pieces (6 and 7) surrounding it. These pieces are formed by cutting just through the support layer (4) leaving the backing layer intact. The central area of the sheet material is removed to provide an opening (8) which is adapted to be fitted around the stoma. The opening may be from 1.5 to 5.0 cm in diameter and is operative to fit around a stoma. The hole may be enlarged subsequently if desired. The ostomy flange is attached to the ostomy bag by removing the central circular piece (5) aligning the opening (8) with the opening in the bag and welding the two together either directly or using an intermediate polymer film. The other two pieces (6 and 7) of the support layer may be left in place until the bag has been applied to the body and then removed if desired.

FIG. 2 shows the view of the other side of the sheet material. The release liner (3) covers the adhesive layer and is formed from a stiff silicone coated release paper which has a weight per unit area of 120 gsm. The release liner (3) comprises three portions, a large generally circular central portion (9) and on two opposite edges, two narrow strip portions (10, 11). In use the patient may remove the central portion (9) of the release liner. The flange is applied to the skin and the edge portions (10, 11) are removed and the remainder of the flange adhered to the skin. The remaining pieces of the support layer (6, 7) may then be removed.

FIG. 3 shows a cross-section through an adhesive sheet material of the invention. The backing layer (1) comprises a polyurethane film having a weight per unit area of 35 gsm and thickness 35 μm. The polyurethane may be a polyether polyurethane such as Estane 5714F (Trade mark).

The backing layer (1) is coated on one surface with a adhesive layer (2). The adhesive has a weight per unit area of 43 gsm. The adhesive may be a polyvinyl alkyl ether adhesive such as a polyvinyl ethyl ether pressure sensitive adhesive or an acrylate ester copolymer adhesive such as one of those described in European patent No. 35399 which comprises a copolymer formed by polymerising 47.5 parts by weight of 2-ethyl hexyl acrylate, 47.5 parts of butyl acrylate and 5 parts of acrylic acid. The adhesive layer (2) is covered by a release liner (3) formed from a silicone coated release paper. The non-adhesive coated side of the backing layer (1) is attached to a support layer (4). The release liner (3) adheres more tenaciously to the adhesive layer (2) than the support layer (4) adheres to the backing layer (1).

The stripping loads were measured using the method described hereinbefore with the following results. The stripping load of the support layer from the film was 6 gf/cm and stripping load of the release liner from the adhesive layer was 18 gf/cm.

Figure 4:
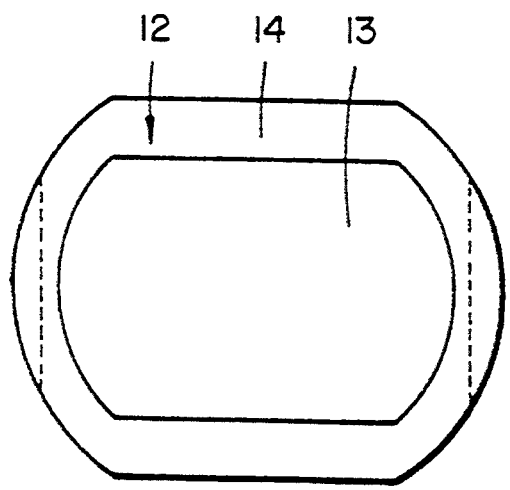
FIG. 4 is an adhesive sheet in the form of an IV dressing which shows the non-adhesive side of the dressing.
Figure 5:
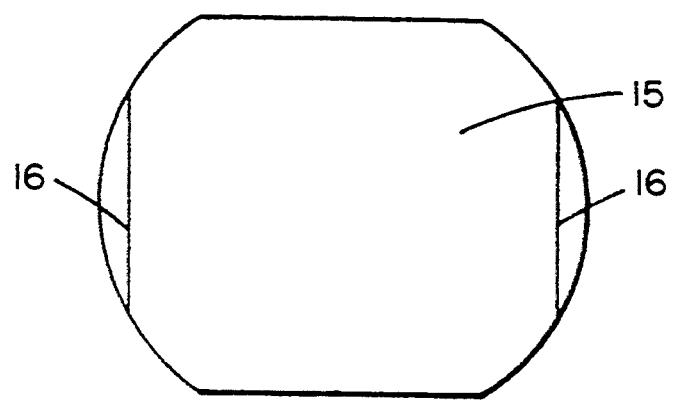
FIG. 5 is an adhesive sheet in the form of an IV dressing which shows the adhesive side of the dressing.

The pressure sensitive adhesive sheet material shown in FIGS. 4 and 5 is in the form of a dressing for retaining an indwelling catheter on the skin. FIG. 4 shows the non-adhesive side of the sheet material. The support layer (12) comprises a release coated paper which has a weight per unit area of 120 gsm. The support layer (12) comprises two pieces a central portion (13) which is generally ellipsoidal in shape. The central area (13) is surrounded by a second piece (14). The pieces are formed by cutting just through the support layer (12). FIG. 5 shows the other side of the sheet material. The release liner (15) covers the adhesive layer and comprises a silicone coated release paper which is separable into three pieces by splitting along the score lines (16).

In use the patient may remove the central piece of the support layer to provide a window through which the injection site may be viewed. The release liner is split at the score lines and the central portion is peeled off. The adhesive sheet material may be applied to the cannula and injection sire. The remainder of the support layer (4) and the remainder of the release liner (15) may be removed if desired.

Figure 6:
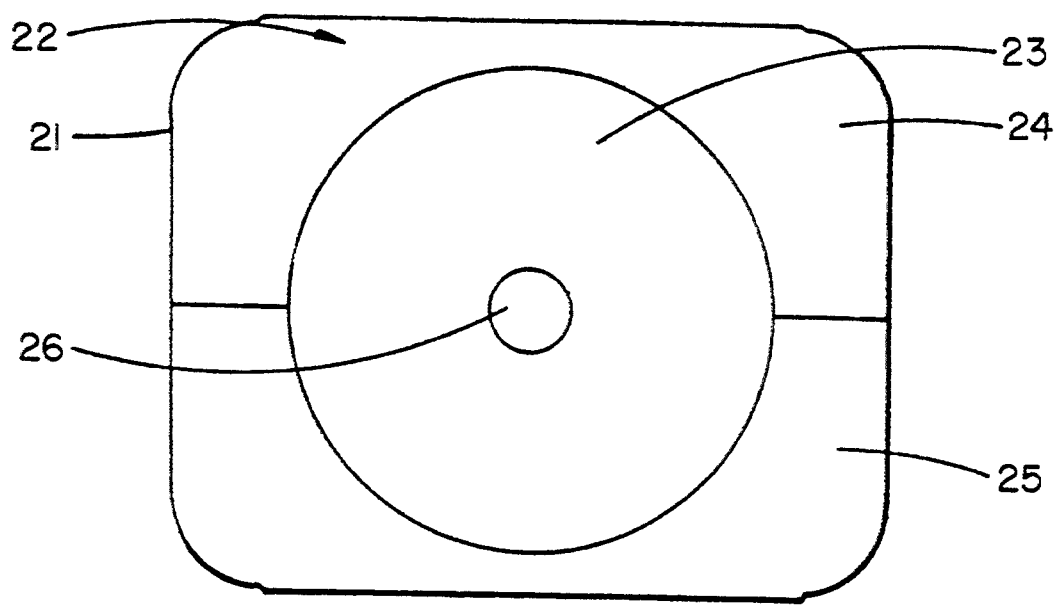
FIGS. 6 and 7 show an alternative arrangement of an ostomy flange.
Figure 7:
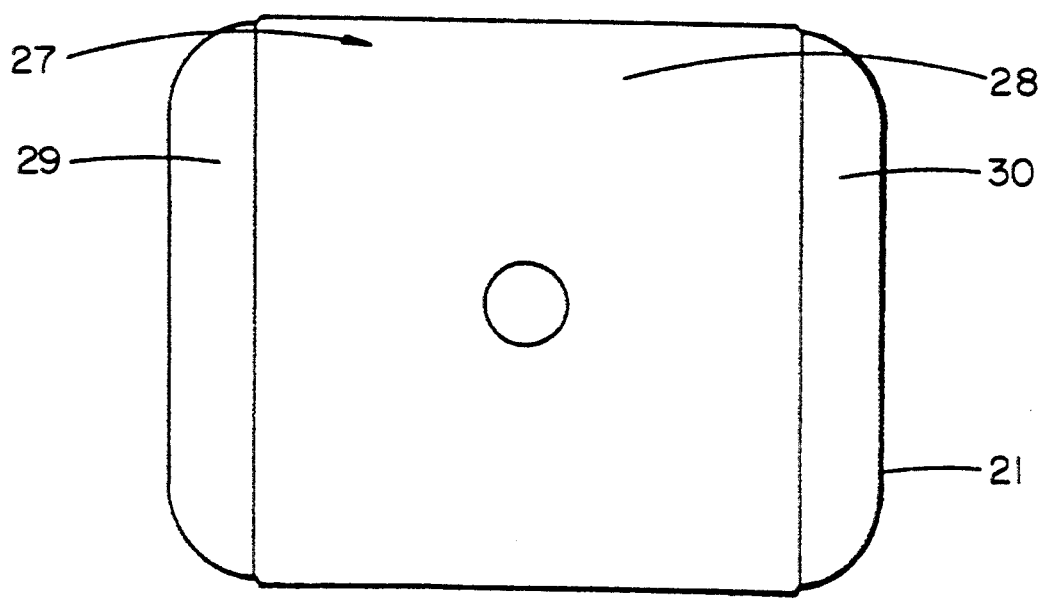

FIG. 6 and 7 show the two sides of an alternative design of an ostomy flange as described in FIG. 1. The overall shape of adhesive sheet material (21) is rectangular with rounded corners. FIG. 6 shows the side which is to be adhered to the ostomy bag in which the support layer (22) which comprises a release coated paper still comprises three pieces, a central circular piece (23) and two arch shaped pieces (24, 25) surrounding it. The central area (26) is removed or is removable and is adapted to fit around the stoma as before.

FIG. 7 shows the other side of the ostomy flange showing the release liner (27) also in three portions, a central portion (28) and two narrow edge portions (29, 30). The method of application of the ostomy flange is as has been described previously.

We claim:

1. An adhesive sheet material for use on the skin which comprises a film backing layer which has upon at least a portion of one surface thereof a pressure sensitive adhesive layer, a removable release liner covering the adhesive layer and a removable support layer attached to the surface of the backing layer remote from the pressure sensitive adhesive layer wherein the stripping load required to separate the release liner from the adhesive layer is at least 25% greater than the stripping load required to separate the support layer from the backing layer and the release liner is stiffer than the support layer.

2. A sheet material as claimed in claim 1 in which the pressure sensitive adhesive layer covers essentially the whole of one surface of the backing layer.

3. A sheet material as claimed in claim 1 in which the stripping load to separate the release liner from the adhesive layer is from 5 to 25 gf/cm.

4. A sheet material as claimed in claim 1 in which the backing layer is moisture vapour permeable and has a moisture vapour transmission rate of at least $500 \text{ g M}^{-2} \text{ 24 h}^{-1}$ at 37° C. and 100% to 10% relative humidity difference.

5. A sheet material as claimed in claim 4 in which the backing layer is a polyurethane film which has a thickness of from 20 to 80 μm.

6. A sheet material as claimed in claim 1 in which the adhesive layer is a polyvinyl alkylether adhesive or an acrylate ester copolymer adhesive and has a thickness of 20 to 40 μm.

7. A sheet material as claimed in claim 1 in which the release liner is a silicone coated release paper which has a weight per unit area of from 100 to 400 gsm.

8. A sheet material as claimed in claim 1 in which the support layer is a conformable paper which has a weight per unit area of 100 to 130 gsm.

9. A sheet material as claimed in claim 1 in the form of an ostomy flange in which a central portion of the sheet is removed or is removable whereby the sheet material is capable of being placed round a stomal opening and the remainder of the support layer comprises a removable central, circular piece, surrounded by peripheral pieces.

10. A sheet material as claimed in claim 1 in the form suitable for covering an indwelling catheter or cannula in which the support layer comprises a central portion which is removable before application to the indwelling catheter or cannula and a peripheral region.

11. A sheet material as claimed in claim 1 in which the backing layer and adhesive layer are translucent.

12. A sheet material as claimed in claim 1 in which the backing layer and support layer are coextensive.

13. A sheet material as claimed in claim 1 in which the adhesive sheet material is sterile and is packaged in a bacteria-proof pack.

* * * * *